(12) United States Patent
Prins et al.

(10) Patent No.: US 7,892,817 B2
(45) Date of Patent: Feb. 22, 2011

(54) MAGNETIC ROTATION TO IMPROVE SIGNAL-OVER-BACKGROUND IN BIOSENSING

(75) Inventors: Menno Willem Jose Prins, Eindhoven (NL); Martinus Barnardus Van Der Mark, Eindhoven (NL); Paulus Cornelis Duineveld, Drachten (NL); Mischa Megens, Eindhoven (NL); Josephus Arnoldus Henricus Maria Kahlman, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 1004 days.

(21) Appl. No.: 11/569,084

(22) PCT Filed: May 13, 2005

(86) PCT No.: PCT/IB2005/051574

§ 371 (c)(1),
(2), (4) Date: Nov. 14, 2006

(87) PCT Pub. No.: WO2005/111596

PCT Pub. Date: Nov. 24, 2005

(65) Prior Publication Data

US 2007/0172890 A1    Jul. 26, 2007

(30) Foreign Application Priority Data

May 18, 2004    (EP)    .................... 04102175

(51) Int. Cl.
*C12M 3/00*    (2006.01)
(52) U.S. Cl. ..................... 435/287.2; 436/526
(58) Field of Classification Search ........... None
See application file for complete search history.

(56) References Cited

U.S. PATENT DOCUMENTS 5,981,297 A    11/1999   Baselt

| | | | |
|---|---|---|---|
| 6,337,215 B1 * | 1/2002 | Wilson | 436/526 |
| 6,787,349 B1 * | 9/2004 | Yamamoto et al. | 435/287.2 |
| 7,048,890 B2 * | 5/2006 | Coehoorn et al. | 422/82.02 |
| 2002/0166760 A1 * | 11/2002 | Prentiss et al. | 204/155 |
| 2004/0058458 A1 * | 3/2004 | Anker et al. | 436/526 |
| 2005/0035757 A1 * | 2/2005 | Prins et al. | 324/204 |
| 2006/0205093 A1 * | 9/2006 | Prins | 436/526 |

FOREIGN PATENT DOCUMENTS

WO    03054523 A2    7/2003

OTHER PUBLICATIONS

Assi, Fabiano et al "Massively Parallel Adhesion and Reactivity Measurements using Simple and Inexpensive Tweezers" Journal of Applied Physics, vol. 92, No. 9, Nov. 2002, pp. 5584-5586.
Harada, Yoshie et al "Direct Observation of DNA Rotation during Transcription by *Escherichia coli* RNA Polymerase", Nature, vol. 409, Jan. 2001, pp. 113-115.
Perrin, A. et al "Immunomagnetic Concentration of Antigens and Detection based on a Scanning force Microscopic Immunoassay" Journal of Immunological Methods, vol. 224, 1999, pp. 77-87.
Rife, J.C. et al "Design and Performance of GMR Sensors for the Detection of Magnetic Microbeads in Biosensors" Sensors and Actutators, vol. A107, 2003, pp. 209-218.
Schmitz, Kenneth S. et al "The Role of Orientation Constraints and Rotational Diffusion in Biomolecular Solution Kinetics", The Journal of Physical Chemistry, vol. 76, No. 4, 1972, pp. 534-545.

* cited by examiner

*Primary Examiner*—Ann Y Lam

(57) ABSTRACT

A method and a device are provided for distinguishing a specific binding from a less specific binding between at least one magnetic nanoparticle and a surface of another entity by applying a magnetic field and detecting a physical parameter relating to magnetic nanoparticle rotational or motional freedom while the magnetic nanoparticle is attached to the surface. The method and device may be applied to in-vivo and in-vitro biomolecular diagnostics. The sensor combines in one sensor the detection of magnetic particles or labels and determination of the binding quality and the properties of magnetic particles or labels which are bound to the surface of another entity.

6 Claims, 9 Drawing Sheets

MAGNETIC ROTATION TO IMPROVE SIGNAL-OVER-BACKGROUND IN BIOSENSING

The present invention relates to the field of detection or diagnostics especially bio-molecular diagnostics, such as medical and food diagnostics for both in vivo and in vitro application. More particularly, the invention relates to a method and device for detecting target molecules in a sample fluid such as a liquid or liquid medium, i.e. both in vivo and in vitro, and for distinguishing a specific binding from a less specific binding between magnetic nanoparticles and a surface of another entity.

The challenge of biosensing is to detect small concentrations of specific target molecules (such as e.g. tumor markers and pathogen-derived material-in the pmol/L range and lower) in a complex mixture (e.g. blood, cell culture, tissue) with high concentrations of e.g. mmol/L of background material (e.g. proteins such as albumin).

Biosensors generally employ a surface 1 with specific capture molecules 2, 3 and labels 4 to facilitate detection. This is illustrated in FIG. 1, which shows a biosensor surface 1 to which first capture molecules 2 are coupled. In the solution 5 targets 6 and labels 4 to which second capture molecules 3 are coupled are present. The targets 6 and labels 4 are allowed to bind to the biosensor surface 1. In FIG. 2 some examples of possible binding geometries of labels 4 to a biosensor surface 1 are illustrated. For example, Type 1 is a desired specific binding and more particularly is an architecture in which the target molecule 6 is sandwiched between a first capture molecule 2 on the biosensor surface 1 and a second capture molecule 3 present on a label 4. Furthermore, labels 4 can also attach to the surface 1 of the biosensor in a non-specific manner, i.e. bind to the surface 1 without mediation of the specific target molecule 6. Type 2 in FIG. 2 represents a single non-specific bond between [the label 4 and/or a second capture molecule 3 coupled to the label 4] and [the biosensor surface 1 and/or a first capture molecule 2 coupled or bound to the biosensor surface 1]. Type 2b is also called cross-reactivity. Normally, a Type 2 kind of binding is weakly bound to the surface 1 and can be removed by stringency procedures such as e.g. washing or magnetic forces. Type 3 in FIG. 2 represents multiple non-specific bonds across a larger area between [the label 4 and/or a second capture molecule 3 coupled to the label 4] and [the biosensor surface 1 and/or a first capture molecule 2 coupled or bound to the biosensor surface 1]. Type 3 kind of bonds are more strongly bound to the surface than Type 1 bonds. Type 4 in FIG. 2 illustrates a degenerate version of Type 1, where the label 4 is bound to the biosensor surface 1 by specific as well as non-specific bonds.

FIG. 3 illustrates biosensing with a label 4 bound to a target 6 embedded in a surface 7. The target 63 can for example be a receptor molecule on a cell membrane, or a protein or another biological molecule in a tissue. This situation arises for example in molecular imaging with dedicated contrast agents, where again specific biological binding is required. The presence or concentration of labels 4 is related to the presence, concentration, or activity of target molecules 6. Imaging can be performed by several ways known in the art, e.g. scanning the excitation field, using a place-dependent excitation, scanning the sensing system, scanning the entity under investigation, using a sensor array, etc.

In order to improve the detection limit and the specificity of capture-based biosensing, it is important to develop technologies that can distinguish populations of different label-binding type. A known solution to reduce non-specific signals is by applying stringency procedures, either chemically (e.g. wash with high salt concentrations) or physically (e.g. temperature, shear flow, magnetic forces). The stringency steps aim at removing weakly bound labels (e.g. Type 2 in FIG. 2) while leaving the specific binding (Type 1 in FIG. 2) undisturbed. As such, the specific-over-background ratio is increased. However, labels 4 that are bound to the biosensor surface 1 according to Types 3 and 4 remain on the surface 1, when these labels 4 are more strongly bound to the surface 1 than a specific bond according to Type 1. This is an important issue for nano-particle labels 4, which have a large surface area available for non-specific interactions ['High-fluorescence nano-particles', Perrin et al., J. Immunological Methods 224, 77 (1999)]. Non-specific binding of magnetic nano-particle labels is also a known problem in GMR biosensors [Rife et al., Sens. Act. A107, 209 (2003)].

A known research method to investigate mechanical properties of biological molecules and molecular bonds is the so-called magnetic tweezer [e.g. Harada et al., Nature vol. 409, p. 113 (2001); Assi et al., J. Appl. Phys. Vol. 92, p.5584 (2002)]. The instrument is based on applying magnetic forces and magnetic rotation to a magnetic particle, with a biological molecule attached to the particle on one end and a static surface on the other end. Typically, the magnetic particle has a diameter between 1 and 5 µm and a magnetic moment of the order of $10^{-13}$ A·m². The magnetic field is applied by mechanical control of an external magnet, typically with a field of 0.1-1 T and a field gradient up to $10^3$ T/m. The force F on a magnetic bead then equals:

$$F = \nabla(m \cdot B) \cong m \nabla B \qquad (1)$$

with m the magnetic moment of the bead or magnetic nano-particle and B the magnetic field. The right-hand approximation applies for a constant particle moment, caused for example by magnetic saturation. Magnetic tweezer experiments are generally used to study single molecules at applied forces in the pN and nN range. Low-frequency molecular rotation and molecular torsion are studied by rotating the external magnet. Optical detection of the bead allows measurement of bead displacement. The applied force can be determined via optical imaging of the thermal vibrations of the bead.

This method, however, has the following limitations. Firstly, it is difficult to translate the instrument into a compact, miniaturized and easy-to-use biosensor array for practical applications. Secondly, the beads that are used are large to have a sufficiently high magnetic moment and to facilitate optical detection. In a biosensor, however, the bead size is preferably lower than 1 micrometer, and more preferred below 500 nm, for fast diffusion, low sedimentation, high surface-to-volume ration, and low steric hindrance on the sensor. Furthermore, the magnetic tweezer technique is generally applied to study single molecules in a research environment. In a practical biosensor there will be many more labels, e.g. more than 100 labels to have meaningful statistics, with densities between 100/mm² and 1000/µm². A further disadvantage is that in current magnetic tweezers, rotational investigations are limited to low frequencies, typically 1 Hz, and it is very difficult to detect the rotational state of the bead. High-frequency measurements are difficult to perform due to the relatively slow and inaccurate optical imaging.

It is an object of the present invention to provide a method and device for detection of target molecules in a mixture with high concentrations of background material with improved signal-to-background ratio.

The above objective is accomplished by a method and device according to the present invention.

In a first aspect of the invention, a sensor device is provided for distinguishing a specific binding from a less specific binding between at least one polarizable or polarized nanoparticle label and a surface of another entity. The sensor device comprises:

- at least one electric or magnetic field generating means for applying an electric or a magnetic field to a sample fluid containing polarized or polarizable, e.g. magnetic nanoparticle labels,
- at least one magnetic sensor element and
- detection means for detecting a parameter related to nanoparticle rotational or motional freedom while the nanoparticle labels are attached to the surface for distinguishing a specific binding from a less specific binding between the nanoparticle labels and a surface of the other entity.

An advantage of the device according to the invention is that it allows to distinguish between different types of label-binding on a surface of another entity such as a biosensor surface or different label-binding populations on a surface of another entity, such as e.g. a bead, a cell, a sensor surface, a tissue, . . . .

The electric or magnetic field generating means may generate a rotating magnetic field. In another embodiment, the electric or magnetic field generating means may generate a unidirectional or one dimensional magnetic field, e.g. a pulsed unidirectional magnetic field, or a sinusoidally modulated field. In this case, the motional freedom may be related to the speed of translation in a certain direction through a fluid, e.g. a liquid or a gas.

The electric or magnetic field generating means may be located on the sensor device and may for example be a current wire or a two-dimensional wire structure. The magnetic sensor element may be one of an AMR, a GMR or a TMR sensor element.

In one embodiment of the invention, the device may comprise two electric or magnetic field generating means positioned at either side of one magnetic sensor element, i.e. e.g. left and right or above and below.

In another embodiment, the sensor device is positioned in between two current lines. In that way, magnetic cross-talk to the magnetic sensor may be minimized. The current lines may for example be parallel current sheets. An advantage is that the magnetic sensors according to this embodiment of the invention, are partially or completely insensitive to the current running through the current sheets and only feel the magnetic field due to the presence of a magnetic particle. By placing the magnetic field sensor in this volume avoids possible saturation of the sensor in case the current is present while the sensor measures the field from magnetic particles.

The present invention also includes a sensor device (10) for distinguishing different types of nanoparticle labels or for distinguishing clusters of nanoparticle labels from single nanoparticle labels, the sensor device (10) comprising:

- at least one electric or magnetic field generating means (14) for applying an electric or a magnetic field to a sample fluid containing polarized or polarizable nanoparticle labels (11),
- at least one magnetic sensor element (15) and
- detection means for detecting a parameter related to nanoparticle rotational or motional freedom to thereby distinguish between different types of nanoparticle labels or to thereby distinguish a cluster of nanoparticle labels from a single nanoparticle label.

The detection means may be optical, magnetic or electrical. The advantage of the method and sensor is that unwanted clusters or nanoparticles such as beads can be distinguished automatically without having to rely on physical separation steps or visual observation, e.g. through a microscope.

In a further aspect of the invention, a method for distinguishing a specific binding from a less specific binding between at least one polarized or polarizable, e.g. magnetic nanoparticle and a surface of another entity is provided. The method comprises:

- providing at least one nanoparticle label,
- applying an electric or magnetic field, and
- detecting a physical parameter relating to nanoparticle rotational or motional freedom while the at least one nanoparticle label is attached to the surface to thereby distinguish the specific from a less specific binding between the nanoparticle label and the surface.

An advantage of the present invention is that it distinguishes between different types of label-binding on a surface of another entity such as a biosensor surface or different label-binding populations on a surface of another entity, such as e.g. a bead, a cell, a sensor surface, a tissue, etc.

Another advantage is that the method of the present invention discriminates between a population having a specific binding and a population having less specific binding and/or between populations with single specific bonds and populations with multiple less specific bonds.

Providing magnetic nanoparticle labels may comprise providing ferromagnetic nanoparticles. The torque that exists between the magnetic moment and the magnetic particle material is due to the magnetic anisotropy of the magnetic particle, which generates an internal magnetic field, and the magnetic roughness of the particle, which generates an internal friction. Ferromagnetic particles have a large magnetic anisotropy energy with respect to the thermal energy, so $K \cdot V > k_B \cdot T$. When the magnetic anisotropy energy is also larger than the magnetic dipole energy in the applied field, i.e. $K \cdot V > m \cdot B$, then the particle orientation and moment orientation are strongly coupled.

In another embodiment of the invention, other magnetic particles other than ferromagnetic nanoparticles may be used, e.g. particles with a variable angle between the orientation of the particle and the orientation of the magnetic moment on the relevant timescales (e.g. the period of the magnetic field modulation), such as superparamagnetic particles.

According to the invention, the applied electric or magnetic field may be a rotating magnetic field. Rotation of beads may for example be used to optimize the exposure rate in a biochemical assay, in other words, the hit-and-stick rate or the effective binding rate ($k_{on}$). When labels are rotated with respect to another body, e.g. the surface of a biochip or the surface of a cell, the interaction and binding rate between the label and the other body can be enhanced.

In another embodiment, the applied electric or magnetic field may be a unidirectional or one dimensional magnetic field, such as for example a pulsed unidirectional magnetic field. In this case, the motional freedom may be related to the speed of translation in a certain direction through a fluid, e.g. a liquid or a gas.

Detection of a physical parameter relating to magnetic nanoparticle rotational or motional freedom may, according to the invention, preferably be performed magnetically. Alternatively, optical detection may be performed, but optical detection of rotation may require the inclusion of optical labels in or on or near the magnetic nanoparticles, with the optical labels or their optical excitation being oriented with respect to the magnetic anisotropy axis of the nanoparticles. In case of optical detection, the mechanical excitation of the label, by magnetic or electrical forces, will modulate the signal from an optical element in the biological complex that is bound to the surface. In one example, label rotation may change the optical signal because the optically-active element has an axis of polarization. In another example, the motion of the optical element may cause in-coupling and/or optical out-coupling with a changing efficiency in an optical evanescent field. In yet another example the motion of the optical element causes a different distance or orientation with respect to an optically perturbing element, e.g. a surface, quenching elements, or enhancing elements such as e.g. plasmonic nanoparticles. Analysis of the modulation of the optical signal may be used to further increase the SNR ratio, because the optical signal from the labels will modulate according to the label actuation. Background signals may be suppressed, e.g. because the autofluorescence of the biological environment will not modulate with the label actuation. Alternatively, the optical signal may be generated by chemiluminescence or electrochemiluminescence, while the optical signal may be modulated by the actuation of the label. Detection may also be performed by an electrical current or voltage, e.g. when a redox enzyme is used as a detection label. Again, modulation of the electrical signal may be caused by actuation of the label. Furthermore, luminescence polarization detection could be used, with long-lifetime labels such as optically-active rare-earth complexes. Also magneto-optical effects could be used for detection, such as Kerr rotation, circular dichroism, etc. Furthermore, detecting a physical parameter relating to magnetic nanoparticle rotational or motional freedom is performed by measuring signal relaxation as a function of time.

The method according to the invention may furthermore comprise providing the magnetic nanoparticle labels with coupling or linking moieties with an internal rotational freedom, e.g. linker molecules with a free carbon-carbon bond, or e.g. an oligo-alkane or oligo-ethyleneglycol chain, in order to enhance the rotational freedom. Other examples of linker molecules may be found in "Polymer Chemistry", by Hiemenz, P. C. Dekker, New York, 1984. Due to the rotational degree of freedom, the magnetic particle labels in binding situations of Type 1 will be free to rotate, while the rotation of labels in bindings of Type 3 and 4 will be strongly hindered. In that way, distinguishing between a specific and a less specific binding may be improved.

The rotational behavior or motional freedom of the magnetic particles will depend on the strength of local viscous friction and on the presence of binding to the surface of the other entity. Furthermore, the rotational behavior or motional freedom of the magnetic particles will depend on the kind of binding. By using the method of the present invention, it is hence possible to detect at the same time different target molecules and different complexes that contain target molecules.

The method according to the invention may be used in bio-molecular diagnostics, either in in vivo or in in vitro bio-molecular diagnostics.

Furthermore, the method according to the invention may be used for distinguishing magnetic particles with different properties, e.g. different magnetic moment and/or rotational friction properties. Rotation spectroscopy may thus be used to perform bead multiplexing, i.e. distinguish beads or magnetic particles with a different intrinsic property.

It is furthermore advantageous that the method according to the invention may be applied to an array of biosensors or a so-called biochip, or in imaging with 3D resolution.

The present invention also includes a method for distinguishing different types of nanoparticle labels or for distinguishing clusters of nanoparticle labels from single nanoparticle labels, the method comprising:

providing nanoparticle labels (11), applying an electric or magnetic field, and detecting a physical parameter relating to nanoparticle rotational or motional freedom to thereby distinguish between a cluster of nanoparticle labels and a single nanoparticle label. The detecting may be by optical, magnetic or electrical methods. The nanoparticle size may range between 1 nm and 5 µm and may preferably be between 5 nm and 500 nm.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
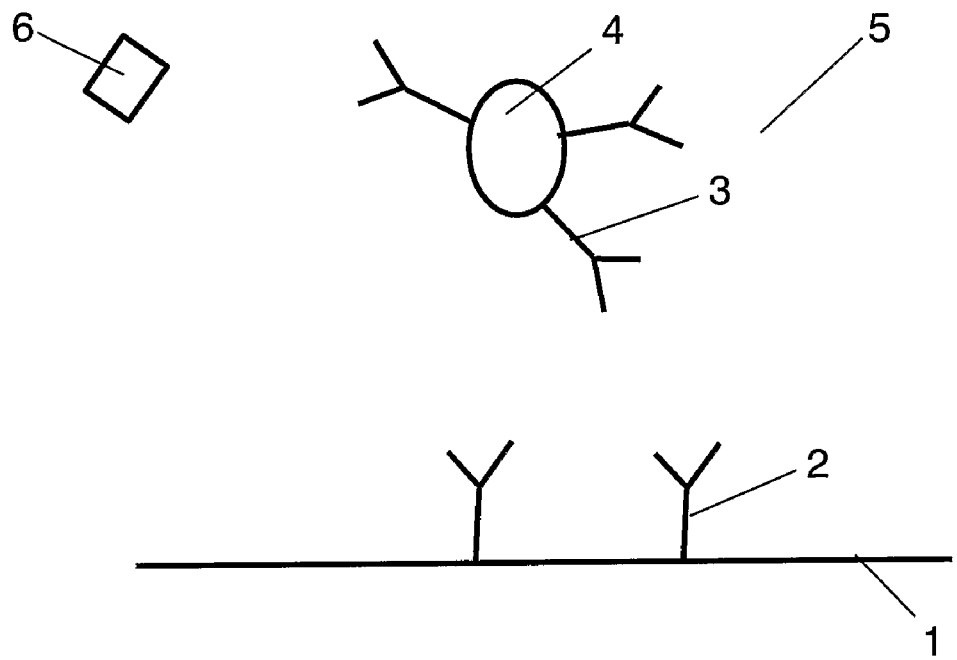
FIG. 1 illustrates a biosensor surface to which first capture molecules are coupled in a solution comprising targets and labels to which second capture molecules are coupled.

In the different figures, the same reference figures refer to the same or analogous elements.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

The present invention provides a sensor 10, such as e.g. a biosensor-array wherein labels are located so that they are influenced by a field generated by a field-generating means, which may for example be a rotating magnetic field generating means including a conductor (e.g. current wires) or an electric field generating means, as well as to at least one magnetic-field sensor element, which may for example be a GMR or TMR or AMR sensor element.

In one aspect of the present invention, the applied electric or magnetic field is such that it generates a torque on the labels. In that way, the labels are rotated with respect to another body (e.g. another bead, a chip, a cell, a tissue) using a magnetic or an electric field. The labels contain magnetic material. The label may, for example, be a magnetic bead, a magnetic particle, a magnetic rod, a string of magnetic particles, or a composite particle, e.g. a particle containing magnetic as well as optically-active material, or magnetic material inside a non-magnetic matrix. In the further description, the labels will be referred to as labels, magnetic nanoparticles or beads and nanoparticles. A parameter relating to the rotational or motional freedom of the nanoparticles in their bound condition is then detected by the sensor elements. The method according to the invention allows high-frequency motional freedom or rotational freedom measurements. Although a strength of a binding can be found by methods which measure detachment forces of labels from another object, such methods do not necessarily determine whether a binding which does not break is a specific binding or some other type of binding. The methods of the present invention provide additional information as to a motional or rotational freedom of bound labels and can thereby confirm more accurately that a binding is specific. Thus, the present invention provides enhancement of the signal-to-background ratio in biosensors, and hence enhancement of the specificity of the biosensor.

Figure 4:
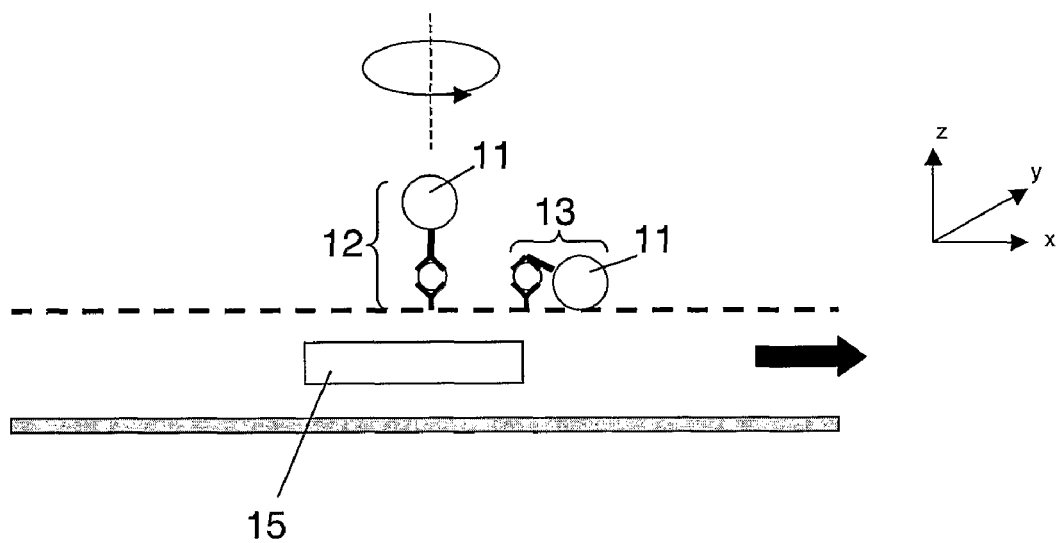
FIG. 4 illustrates the difference between a rotatable and a fully immobilized nanoparticle on a sensor surface.

The sensor 10 according to the present invention combines in one sensor 10 the detection of nanoparticles or labels bound to a surface of another entity, such as e.g. another bead, a cell, a sensor surface, tissue . . . and the determination of the binding quality and the properties of the magnetic particles or labels 11 in a three-dimensional xyz space around the sensor 10. In order to distinguish between a rotatable label 12 and a fully immobilized label 13 (FIG. 4), measuring the three-dimensional rotational potential (around the x-axis, y-axis and/or z-axis) is a valuable method (see further).

The method and device of the present invention will be described by means of labels or nanoparticles 11 which are bound to a sensor surface. However, this is not limiting to the invention. As already mentioned, the method and device of the present invention may also be applied when labels or nanoparticles 11 bind to a surface of other entities, such as e.g. a tissue or cells. Furthermore, the method and device of the invention may be applied to in vivo and in vitro biomolecular diagnostics.

The applied magnetic field should be large enough to generate an orientation of the magnetic moment in the particles 11. The required field depends on the size and on the type of particle 11, e.g. superparamagnetic, ferromagnetic, spherical or non-spherical. For example, superparamagnetic particles with a diameter of 100 nm, can have a saturated magnetic moment m of about $10^{-16}$ A·m$^2$, while superparamagnetic particles with a diameter of 1 μm may have a saturated magnetic moment m=$10^{-13}$ A·m$^2$. On the other hand, particles made out of high-density magnetic material having a diameter of 100 nm may have a saturated magnetic moment m of $10^{-15}$ A·m$^2$.

The magnetic torque τ applied to a magnetic nanoparticle or bead with magnetic moment m, by applying a rotating magnetic field, is given in equation 2 [see Reitz et al., 'Foundations of electromagnetic theory', chapter 8, Addison-Wesley, $3^{rd}$ ed. (1979)]:

$$\bar{\tau} = \bar{m} \times \bar{B} \quad (2)$$

The torque on the magnetic moment of the bead or magnetic nanoparticle orients the moment of the bead or particle toward a parallel orientation with the applied magnetic field. In a biosensor, the applied torque is opposed by a torque due to (i) rotation of the magnetic moment with respect to the particle itself, (ii) rotation of the particle with respect to a viscous environment in which the particle resides, and (iii) forces from particle binding to the surface of the biosensor:

$$\tau_{appl} = \tau_{magn} + \tau_{viscous} + \tau_{binding} \quad (3)$$

For small particles 11 in liquids, inertial forces can generally be neglected with respect to viscous forces. This means that resonances are damped and that the mass of the particle 11 is not important in the equation of motion. For example, the time to reach the steady state after application of a torque is approximately given by $\rho R^2/3\eta$, with ρ the mass density of a particle, R the particle radius, and η the viscosity of the fluid. For a particle with density $1.5 \cdot 10^3$ kg/m$^3$, R=50 nm and $\eta = 10^{-3}$ Pa·s, a time-to-steady-state of about one nanosecond may be achieved, which is generally much shorter than the rotation period of the particles 11 (see further).

In the case that the present invention is used with gaseous fluids it may not be accurate to neglect the inertial forces with respect to viscous forces and a more complete analysis is necessary.

Figure 3:
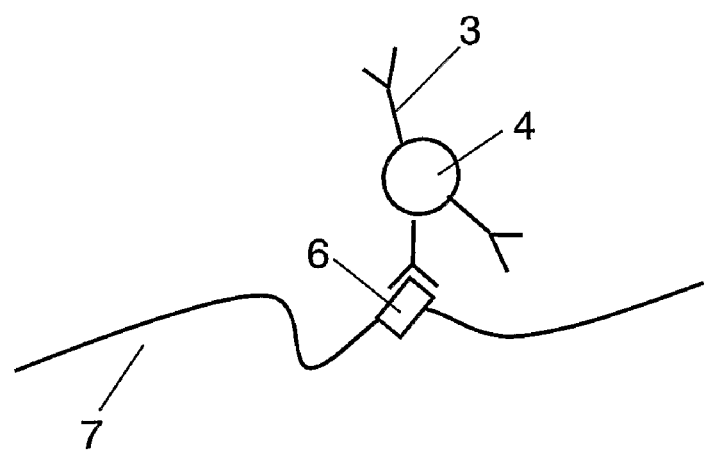
FIG. 3 illustrates how a label can bind to a target embedded in a surface, e.g. a receptor molecule on a cell membrane, or target molecule on a tissue surface.

Assuming that the magnetic field B and the magnetic moment m of a particle are located in a same plane, e.g. the xz-plane, the vector of field B is in this plane aligned according to angle $\phi_B$ with a reference axis, e.g. with the x-axis as illustrated in FIG. 3, and m is in this plane aligned making an angle $\phi_m$ with the reference axis, e.g. the x-as in FIG. 3. The applied torque is then:

$$\tau_{appl} = mB \sin(\phi_B - \phi_m) \quad (4)$$

The torque that exists between the magnetic moment and the magnetic particle material is due to the magnetic anisotropy of the magnetic particle, which generates an internal magnetic field, and the magnetic roughness of the particle, which generates an internal friction. For simplicity, it is assumed that the magnetic particle has an ellipsoidal shape with uniaxial symmetry, having its anisotropy axis making an angle $\phi_p$ with a reference axis, e.g. the x-axis:

$$\tau_{magn} = KV\sin(\varphi_m - \varphi_p) + \gamma \frac{d(\varphi_m - \varphi_p)}{dt} \quad (5)$$

with K the magnetic anisotropy (units J/m³), V the magnetic volume of the particle and γ the magnetic friction coefficient.

The viscous torque is determined by the rotational friction of the environment. In case this is dominated by the solution with viscosity η, the viscous torque is approximately equal to:

$$\tau_{viscous} = \pi\eta d^3 \frac{d\varphi}{dt} \quad (6)$$

with d the hydrodynamic diameter of the particle. The presence of a surface near the particle, as is the case in bio sensors, may cause some deviation from equation (6). The torque due to binding of the label to a surface can vary strongly, depending on the kind of label-to-surface binding.

Figure 2:
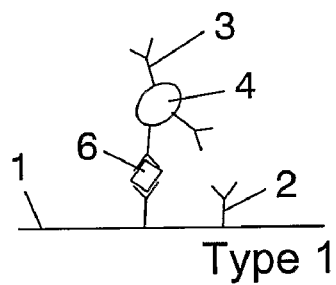
FIG. 2 illustrates different ways of how a label can bind to a biosensor surface.
Figure 2:
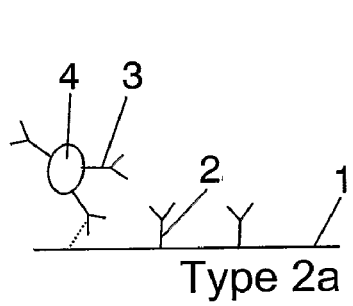
Figure 2:
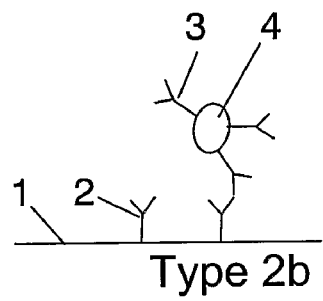
Figure 2:
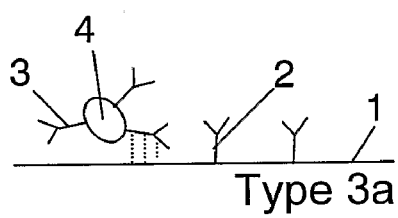
Figure 2:
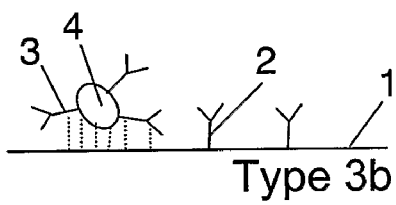
Figure 2:
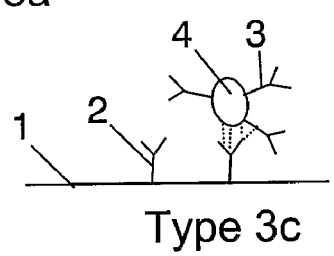
Figure 2:
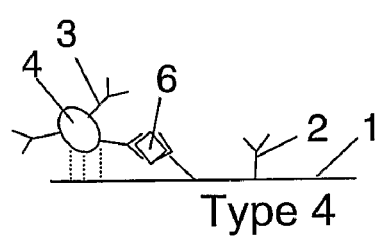

The rotational friction may range from very low (e.g. FIG. 2, Type 1, where the friction can approach the free-in-solution case when a rotatable linker is present, see further) to very high or completely inhibited rotation (e.g. FIG. 2, Type 3b). In the following, the binding energy of a relatively large particle with a diameter of 1 μm and being strongly bound to a surface (near-covalent bond) is estimated. When two materials are covalently bound, the binding energy per unit area is of the order of $10^{-18}$ J/nm²=1N/m. If it is assumed that the particle 11 binds across a large area of e.g. 0.1 μm², the binding energy then becomes 1 N/m×0.1 μm², which equals $10^{-13}$ J. It is now possible to calculate the magnetic torque that can be applied. For example, when a field of 1T is applied to a μm-sized particle with a magnetic moment of $10^{-13}$ A·m², the applied magnetic torque equals $10^{-13}$ J. in other words, with magnetic rotation even very strongly bound labels may be actuated.

Although the present invention is mainly exemplified by reference to magnetic fields and magnetic field generators, the present invention also includes rotating and orienting particles by electrical forces, i.e. by electric fields from electric field generators. The torque on a particle due to electric forces equals:

$$\vec{\tau} = \vec{p} \times \vec{E}, \quad (7)$$

with p the electric dipole moment of the particle and E the applied electric field. As in the magnetic case, the dipole moment can be permanent as well as transient, and it can be due to a non-uniform shape of the particles (e.g. a rod), an electrical polarizability that is different than the surrounding material, ferroelectricity of the used material, (super) paraelectricity of the material, etc.

To know if an electrical torque can orient a particle against thermal randomization, the electric energy is calculated:

$$U = \Phi \frac{1}{2}\varepsilon E^2, \quad (8)$$

where Φ is the volume of the particle, ε the electric polarizability and E the applied electric field. For example, for a 100-nm diameter particle, a polarizability of the order of $10^{-11}$ F/m, and a field in the range E=$10^6$-$10^8$ V/m, we find an electrostatic energy in the range $10^{-21}$-$10^{-17}$ J. In other words, the electrical orientation energy is of the order of or much higher than the thermal energy at room temperature ($k_B$T=$4.10^{-21}$ J).

Fluids surrounding the particles will often be electrically active, for example due to ionic charges, electric dipoles, induced electric dipoles in the material etc. This electrical activity can partially shield the particles from the applied electric field. In addition, the applied fields can cause electrochemical reactions or electric breakdown. Accordingly, it is preferred if the applied fields are time-varying (AC).

In the following description, the method according to the present invention will be discussed by means of different embodiments. However, the invention is not only limited to the described embodiments which are only representative examples of the present invention.

In a first embodiment of the present invention, ferromagnetic particles 11 are used as labels in the detection of target molecules, such as for example proteins or nucleic acids in a biological fluid material, e.g. blood. The ferromagnetic particles 11 may be provided with a first capture molecule as already described with respect to FIG. 1.

Ferromagnetic particles 11 have a large magnetic anisotropy energy with respect to the thermal energy, so K·V>$k_B$·T. When the magnetic anisotropy energy is also larger than the magnetic dipole energy in the applied field, i.e. K·V>m·B, then the particle orientation and moment orientation are strongly coupled. Assuming that $\phi_m=\phi_p$, for ferromagnetic particles 11, which can freely rotate and which are not rigidly or partly bound to a surface ($\tau_{binding}=0$), the equation of motion then becomes (see equation (3) to (6)):

$$m(t)B(t)\sin(\varphi_B - \varphi_p) = \pi\eta d^3 \frac{d\varphi_p}{dt} \quad (9)$$

Assuming that the magnetic field has a constant magnitude and a varying orientation, equation (9) simplifies to:

$$\sin(\varphi_B - \varphi_p) = \frac{d\varphi_p}{d(\alpha t)}, \text{ with } \alpha = \frac{mB}{\pi\eta d^3} \quad (10)$$

If, for example, η=$10^{-3}$ Pa·s, d=100 nm and m=$10^{-16}$ A·m², then α/B equals 31,8 MHz/T. Assuming that a field amplitude of 10 mT is applied, a frequency α is achieved in the order of about 300 kHz. It has to be noted that thermal vibrations may influence a particle and lead to an inaccuracy between the theoretical and the actual angle of about $k_B$T/mB, wherein $k_B$ is the Boltzmann-constant and T the temperature. With T=300 K, m=$10^{-16}$ A·m² and B=10 mT an angle inaccuracy of only 0.2 degrees is present.

Figure 5:
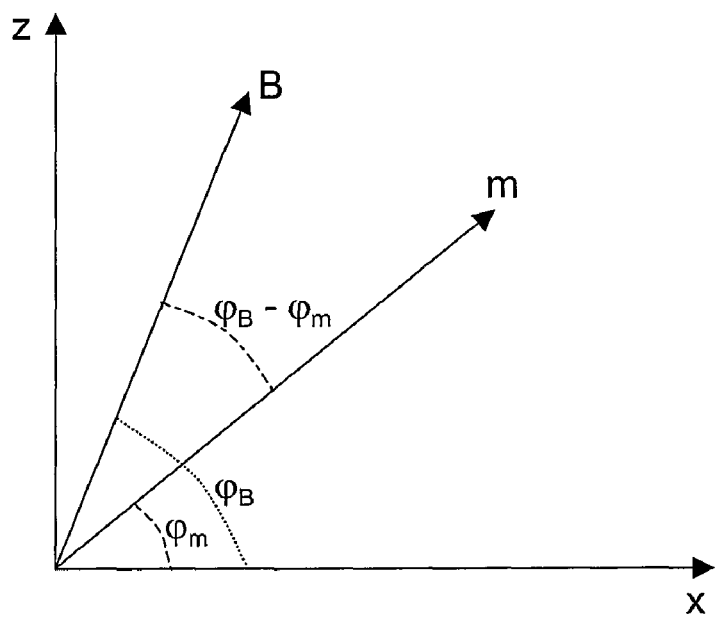
FIG. 5 shows a vector representation of the magnetic field B and magnetic moment M of a particle.

If it is now assumed that the applied magnetic field rotates in the xy plane (see FIG. 5) at angular frequency ω, the magnetic particles 11 will separate into populations with different angular delay Δ=$\phi_B$-$\phi_p$ between field and moment, according to:

$$\sin(\Delta)=\omega/\alpha \quad (11)$$

Ferromagnetic particles 11 with α>ω will follow the field at a definite angular delay. Ferromagnetic particles 11 with α<ω cannot follow the field and loose their net orientation.

Figure 6:
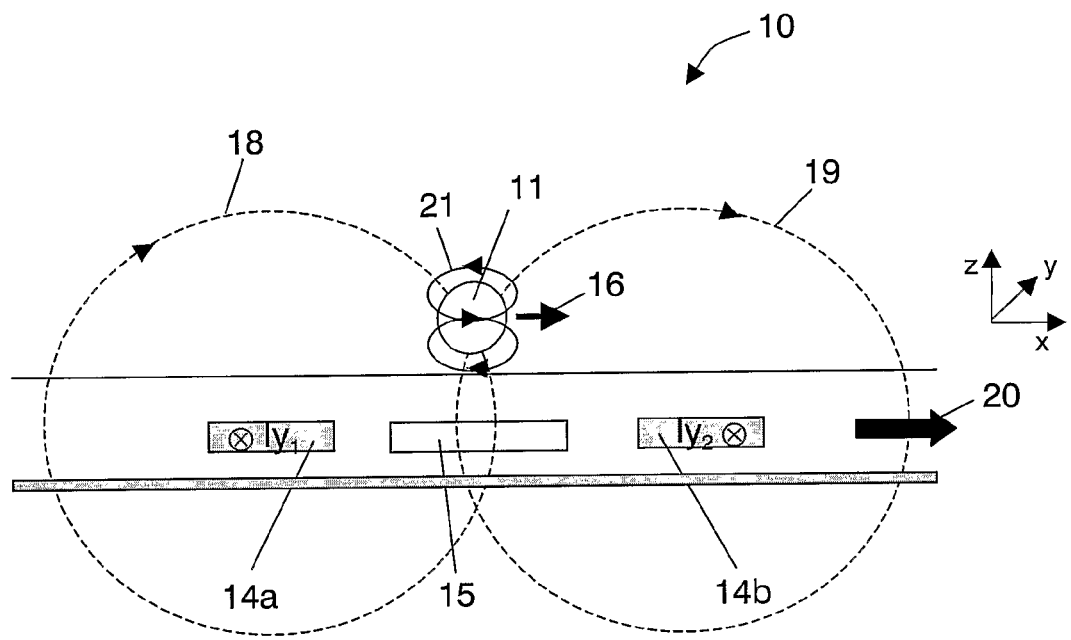
FIGS. 6 and 7 show a magnetic particle close to a field-generating current wire and a magneto-restrictive detector strip according to one embodiment of the present invention.
Figure 7:
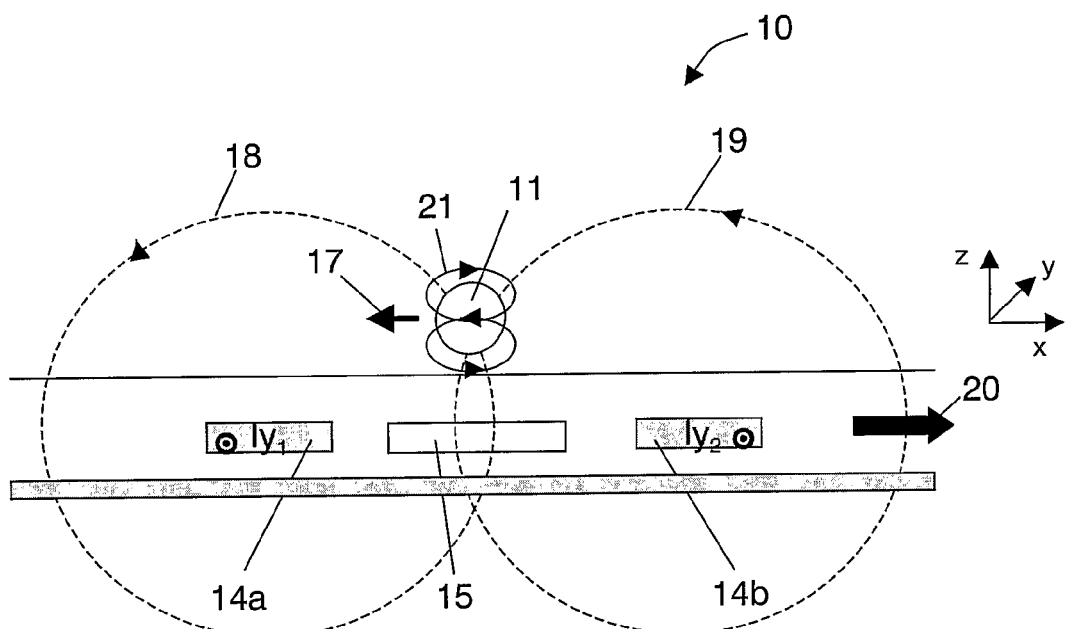

The rotating magnetic field may be applied to the ferromagnetic particles 11 by means of a magnetic field generating means which may, for example, be magnetic materials (rotating or non-rotating) and/or conductors such as e.g. current wires 14 (see FIGS. 6 and 7). In this embodiment, the rotating magnetic field preferably may be generated by means of current wires 14*a,b*. Detection of nanoparticle rotation may preferably be performed magnetically. Alternatively, optical detection may be performed, but optical detection of rotation may require the inclusion of optical labels in or on the magnetic nanoparticles 11, with the optical labels or their optical excitation being oriented with respect to the magnetic anisotropy axis of the nanoparticles 11. Luminescence polarization detection could be used, with long-lifetime labels such as optically-active rare-earth complexes. Also magneto-optical effects could be used for detection, such as Kerr rotation, circular dichroism, etc.

In this first embodiment, the magnetic detection may preferably be performed by using an integrated magnetic sensor 10. Various types of sensor may be used such as e.g. a Hall sensor, magneto-impedance, SQUID, or any other suitable magnetic sensor. FIGS. 6 and 7 illustrate an integrated magnetic nanoparticle sensor 10 comprising a magnetic sensor element 15, which includes a magnetoresistive element, for example, a GMR or a TMR or an AMR sensor element. A rotating magnetic field generator is provided. This may be external to the sensor 10 or integrated within the sensor 10 and can, for example, include two conductors, which in this embodiment may be current wires 14*a* and *b*, each at one side of the magnetic sensor element 15, as well as a current generator for the wires. The magnetic sensor element 15 may for example have an elongated (long and narrow) strip geometry. The rotating magnetic field is thus applied to the ferromagnetic particles or labels 11 by means of current flowing in the integrated current wires 14*a* and *b*. Preferably, the current wires 14*a* and *b* may be positioned in such a way that they generate magnetic fields in the volume. where ferromagnetic particles 11 are present. By applying currents $Iy_1$ and $Iy_2$ in the positive y-direction to the current wires 14*a* resp. 14*b*, as illustrated in FIG. 6, a resultant magnetic field in the positive x-direction, which is indicated by arrow 16, is generated. By inverting the current directions, as illustrated in FIG. 7, the resultant magnetic field flips to the negative x-direction, as indicate by arrow 17. When the volume of the region where a magnetic field is generated is well-matched to the region where labels or nanoparticles 11 are present, then the system will have a minimum inductance, which is useful for low-power operation at high frequencies and at relatively high magnetic fields.

In FIGS. 6 and 7, reference number 18 refers to the magnetic field generated by the first current wire 14*a*. The magnetic field generated by the second current wire 14*b* is indicated by reference number 19. The total magnetic field influencing the magnetic nanoparticle 11 is the sum of the magnetic fields 18, 19 generated by the integrated current wires 14*a* resp. 14*b* and the fields of any remote field-generating components, e.g. coils, magnets and small fields due to the Earth's magnetic field and stray magnetic fields from other devices. The remote field generating components may generate a homogeneous field while nearby field generating components may generate an inhomogeneous field.

The sensor device 10 can have a sensitive direction such that if it is positioned in the xy plane, the magnetic sensor element 15 only detects a component of the magnetic field in a certain direction e.g. the x-component of a magnetic field, as indicated by arrow 20 in FIGS. 6 and 7. In other words, the x direction is the sensitive direction of the sensor 15. Hence, the magnetic fields caused by currents flowing through the conductors 14*a* respectively 14*b*, will hardly or will not be detected by the sensor 15 in the absence of magnetic nano-particles 11 as they are oriented mainly in the z-direction at the location of the sensor 11.

In case magnetic particles 11 are present at the surface of the sensor 10, they each develop a magnetic moment m. The magnetic moments m generate dipolar stray fields which have in-plane magnetic field components 21 at the location of the sensor 10 (FIGS. 6 and 7).

The magnetic sensor element 15 measures fields caused by the orientation of magnetic moments of the magnetic particles 11. The moment orientation is related to the physical orientation of the particles 11, therefore, populations of particles 11 with different rotational behavior or a different motional freedom can be distinguished by the magnetic sensor 15.

The rotational behavior or motional freedom of the magnetic particles 11 will depend on the strength of local viscous friction and on the presence of binding to the surface of the sensor 10, which is the case in this embodiment, or to a surface of another entity. Furthermore, the rotational behavior or motional freedom of the magnetic particles 11 will depend on the kind of binding, some of which have already been described in FIG. 2, that occurs at the sensor surface or at the surface of another entity. Therefore, particle populations with different (bio)chemical environments will have different traces in a measured rotation spectrum (e.g. amplitude and phase measured as a function of B and ω). Hence, by using the method of the present invention it is possible to detect at the same time different target molecules and different complexes that contain target molecules.

The method of binding discrimination and population discrimination by the magnetic detection of rotation or motional freedom preferably requires a clear relationship between the physical rotation and magnetization rotation or the physical motional freedom and the motional freedom of the magnetization freedom. For ferromagnetic particles 11 this implies that the applied field should preferably be smaller than the coercive field of the particles in the frequency range of interest.

Furthermore, rotational excitation can be applied along different axes of rotation. The measured spectra can be compared, e.g. to determine the anisotropy of the magnetic nanoparticle environment. For example, measurements with rotation around the z-axis and around the x-axis can distinguish populations of Type 1 and Type 3*a* in FIG. 2. Also, rotation anisotropy may reveal the distance between particle 11 and the surface.

The sensor 10 described in the above embodiment is not limiting to the invention. Also other sensor configurations may be used together with the invention. For example, the sensor 10 may comprise more than two magnetic field generators 14*a* and *b* and may comprise more than one magnetic sensor element 15.

Figure 8:
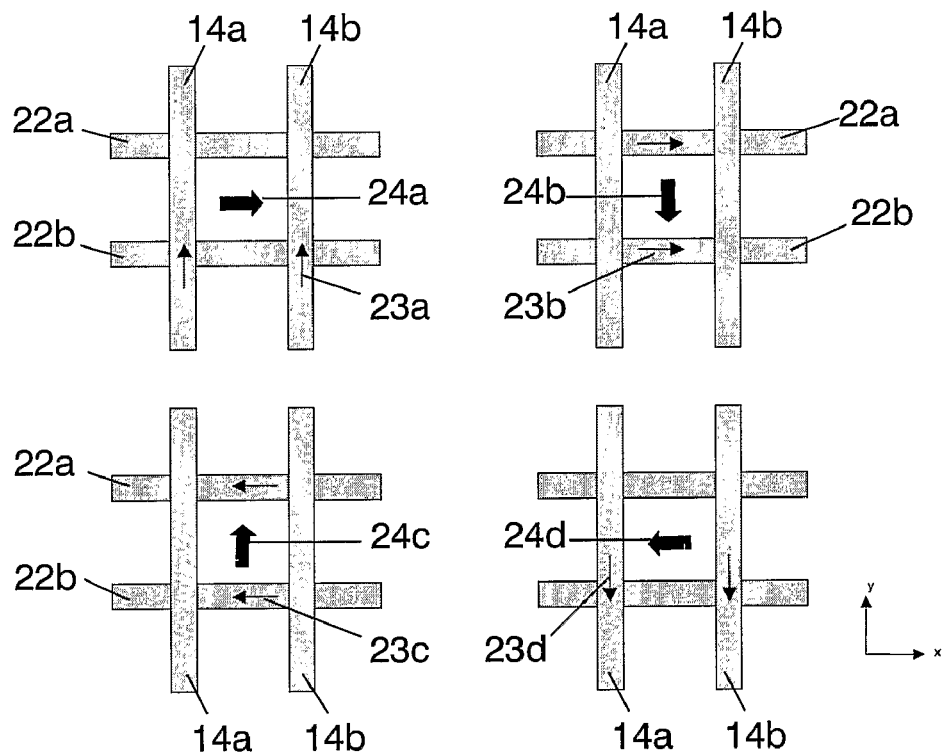
FIG. 8 illustrates a two-dimensional wire structure which may be applied as magnetic field generating means in a sensor according to an embodiment of the present invention.

In a second embodiment, the principle of the first embodiment is extended to a sensor 10 comprising a two-dimensional wire structure as magnetic field generating means, as illustrated in FIG. 8. The two-dimensional wire structure may comprise current wires 14*a,b* in the y-direction and current wires 22*a,b* in the x-direction, which in the further description will be referred to as y- resp. x-wires 14*a,b* resp. 22*a,b*. Depending on the direction of the currents, indicated by arrows 23 *a-d*, in the x- and y-wires 22*a,b* resp. 14*a,b*, the net magnetic field, indicated by arrow 24 *a-d*, rotates in the xy plane, which takes the magnetic particles or beads 11 along. In this way, a so-called four-pole 'bead' motor results. This method is, however, not limited to rotating. When the particles or beads 11 cannot rotate, they are bent or pulled in a certain direction, which can then also be detected. In this way, the binding quality can be measured, hence by measuring the stiffness of the binding. This may be done by measuring the movement into certain directions as a response to the magnetic forces induced by the current wires 14a,b resp. 22a,b. As a simplified example, the magnetic field gradient generated around a single on-chip current wire equals:

$$\frac{dB}{dR} = \frac{\mu_0 I}{2\pi r^2} \quad (12)$$

with I the current through the current wire 14a,b and r the distance from the current wire 14a,b. For example, a current of 10 mA at a distance of 5 μm generates a field gradient of 80 T/m. Assume a bead 11 with a diameter of 100 nm and a magnetic moment of $10^{-13}$ A·m$^2$ in an environment with viscosity 1 mPa·s. Then the translational speed due to the field gradient equals 0.8 mm/s. When the oscillation period is 100 μs, the longitudinal displacement of the bead is about 80 nm, which can be detected.

Furthermore, the existence of rotating particles 11 gives also information on their presence, so that in this way also the detection of particles 11 can be performed. The method according to this second embodiment offers full 3D spatial resolution for detection and rotation/movement of magnetic particles or labels 11.

Figure 9:
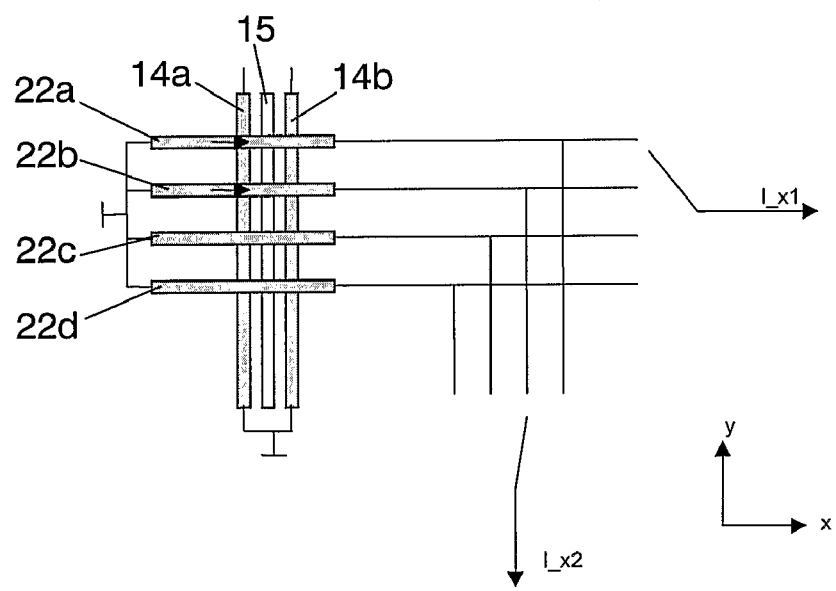
FIGS. 9-12 illustrate possible sensor configurations using two-dimensional wire structures according to an embodiment of the present invention.

In a sensor 10 according to the invention, the two-dimensional wire structures may have different configurations and may be applied in different ways. This is illustrated in FIG. 9 to 12. In FIG. 9, the x- and y-current wires 22a-d and 14a,b are isolated from each other and may be formed out of two different metal layers. A magnetic sensor element 15 is positioned in between the y-current wires 14a,b. By selecting the proper x-current wires 22a-d, nanoparticles 11 at a specific y-position can be rotated. The configuration illustrated in FIG. 9 offers localized detection and rotation of magnetic particles 11 using a single magnetic sensor element 15.

Figure 10:
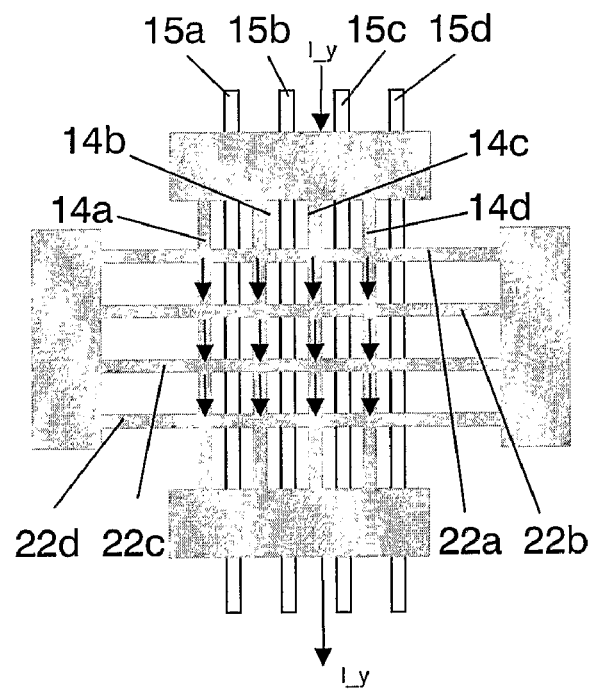
Figure 11:
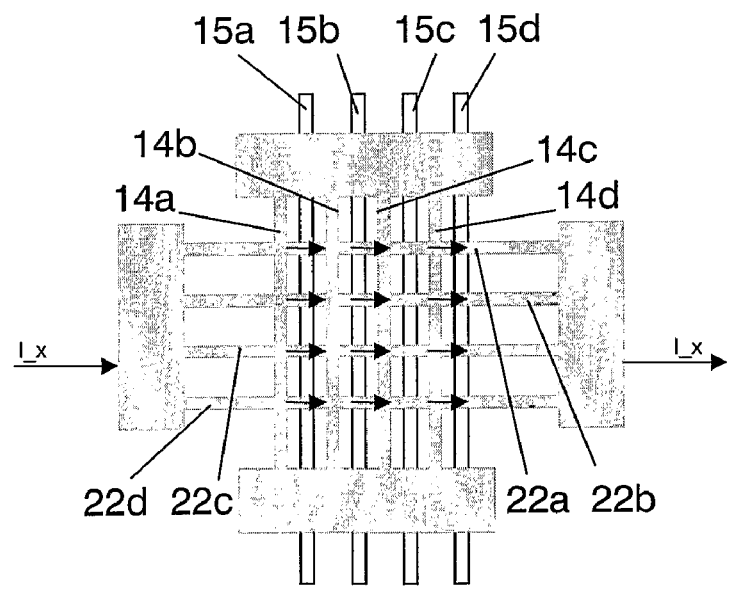

Another possible configuration is illustrated in FIGS. 10 and 11. In this configuration, both the x- and y-current wires 22a-d resp. 14a-d are formed out of the same metal layer. Each magnetic sensor element 15a-d may be positioned in between two y-current wires 14a-d. The currents through the x- and y-current wires 22a-d resp. 14a-d can be controlled individually.

Figure 12:
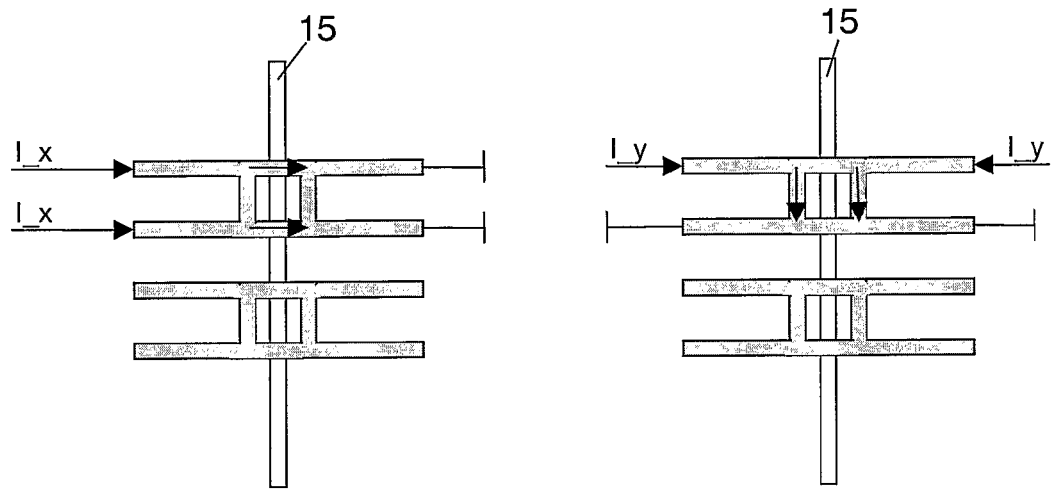

In FIG. 12, still another configuration, through which local bead rotation may be performed, is illustrated. In this configuration, the two-dimensional wire structure is formed out of the same metal layer and is positioned on top of the magnetic sensor element 15. However, in other configurations, the two-dimensional wire structure may also be positioned under the magnetic sensor element 15. In both cases, the two-dimensional wire structure and the magnetic sensor element 15 have to be isolated from each other.

The second embodiment has the advantage that local bead rotation/movement may be achieved. Local bead rotation/movement offers 3D spatial resolution on binding quality at surface and bulk. Furthermore, applying local excitation leads to 3D detection of magnetic nanoparticles 11. Moreover, the second embodiment furthermore has the advantage of low-power consumption due to localized excitation.

Figure 13:
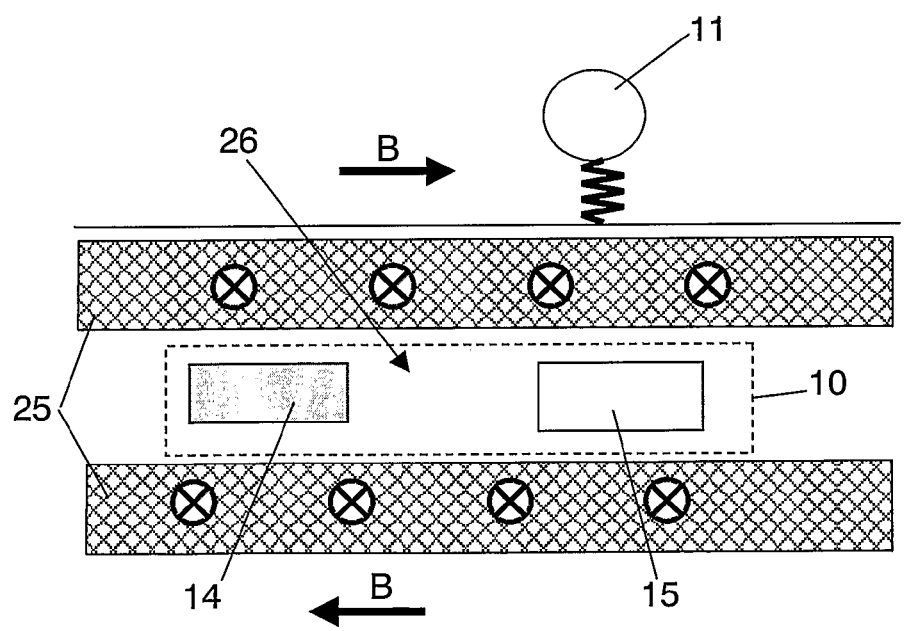
FIG. 13 shows a cross-sectional view of a sensor configuration according to an embodiment of the invention.

In another embodiment according to the invention, magnetic cross-talk to the magnetic sensor 10 is minimized, by providing current lines, which in this embodiment may be current sheets 25, above as well as below the magnetic sensor 10, which makes it possible to create a field-free volume, indicated by arrow 26 in FIG. 13, in which the sensor 10 is located. Therethrough, it becomes possible to measure the field of the magnetic particles 11 simultaneously exerting high torques with strong currents on these particles 11, without saturating the sensor 10. The resulting magnetic field is independent of the distance to the current sheets 25 in the limit that the distance is small compared to the size of the sheet 25 (FIG. 13). If J is the current density, then the magnetic field is given by B=$\mu_0$·J/2. In case a double current sheet is used, as is the case in FIG. 13, a field free volume 26 exists between the sheets 25, as between parallel current sheets 25 carrying the same current, there is no magnetic field. The advantage is that the magnetic sensors 10 according to this embodiment of the invention, are completely insensitive to the current running through the current sheets 25 and only feel the magnetic field due to the presence of a magnetic particle 11. Hence, placing the magnetic field sensor 10 in this volume avoids possible saturation of the sensor 10 in case the current is present while the sensor 10 measures the field from magnetic particles 11.

Figure 14:
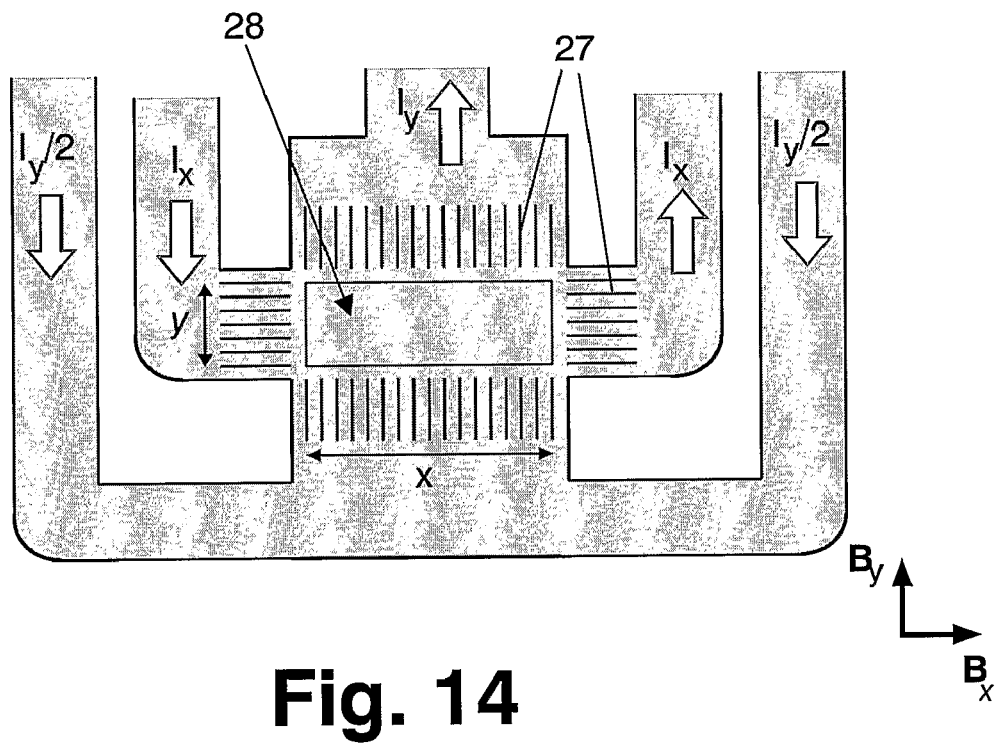
FIG. 14 shows a top view of the sensor configuration of FIG. 12.

The current sheets 25 can be used to rotate a magnetic particle 11 in the xy-plane by applying time varying currents in the x and y direction simultaneously. This is illustrated in FIG. 14 for the example given in FIG. 13. A rotating magnetic field with constant amplitude is obtained if.

$I_x = J_0 \cdot y \cdot \cos \omega t$, and $I_y = J_0 \cdot x \cdot \sin \omega t$ With $J_0 = 2B/\mu_0$ the desired current density. In order to maintain a homogeneous current in each of the sheets, spreading of the current flowing, for example, in the x-direction into the leads carrying the current in the y-direction must be suppressed. This can be done successfully by applying a so-called current comb 27 in each of the current leads. The current combs 27 are used thus to ensure homogeneous flow of current and hence a homogeneous distribution of the magnetic field over the entire sensor area 28. The current comb 27 effectively acts as a set of parallel resistors which reduces the current running parallel to but outside the area of the magnetic sensor 10.

An advantage of the current sheet 25 with respect to series of e.g. parallel wires, even at very high packing density, is that the current can flow in any direction within the sensor area 28, and hence no crossing wires, resulting in an extra layer, are required to allow for rotation of the magnetic field within the sensor area 28. Also, separate current wires give rise to inhomogeneities within the magnetic field, potentially affecting both the field acting on the particles 11 as well as on the sensors 10. Using the current sheets 25, the whole sensor area 28 may homogeneously be addressed.

In still a further embodiment, the rotational or motional freedom difference between particles 11 in specific binding (e.g. FIG. 2, Type 1) versus particles 11 in a less specific binding (e.g. FIG. 2, Type 3b), and hence the sensor specificity, may be enhanced by engineering the rotational freedom. This may, for example, be done by using a magnetic particle label 11 that is free to rotate when it is involved in a single specific bond and by measuring the motional freedom of the label.

There are different ways to engineer a rotational freedom for the labels 11 when they are in a desired binding state, e.g. FIG. 2 Type 1. One way is by providing the capture molecules on the surface with a rotational freedom. Another way is by providing the capture molecules on the nanoparticle 11 with rotational freedom. The capture molecules themselves can have rotational freedom (e.g. in the case of single-chain DNA or RNA strands) or dedicated linkers can be used. To enhance the rotational freedom, linker moieties with a freedom of rotation can be used, e.g. linker molecules with a free carbon-carbon bond, e.g. an oligo-alkane or oligo-ethyleneglycol chain. Examples of linker molecules may be found in "Polymer Chemistry", by Hiemenz, P. C. Dekker, New York, 1984. Due to the rotational degree of freedom, the magnetic particle labels 11 in binding situations of Type 1 will be free to rotate, while the rotation of labels in bindings of Type 3 and 4 will be strongly hindered.

The thermal rotation relaxation rate of the labels 11 may be estimated from the rotational diffusion coefficient $D_r$ (units $s^{-1}$):

$$D_r = \frac{k_b T}{8\pi \eta R^3} \qquad (13)$$

with η the effective viscosity of the fluid near the particle 11 and R the particle radius. In case of for example water (η=1 mPa·s) the rotational diffusion coefficients are summarized in table 1 for different values of R.

TABLE 1

| R [nm] | $D_r$ [Hz] |
|---|---|
| 500 | 10 |
| 100 | $1.3 \times 10^3$ |
| 35 | $30 \times 10^3$ |
| 10 | $1.3 \times 10^6$ |
| 1 | $1.3 \times 10^9$ |

Figure 15:
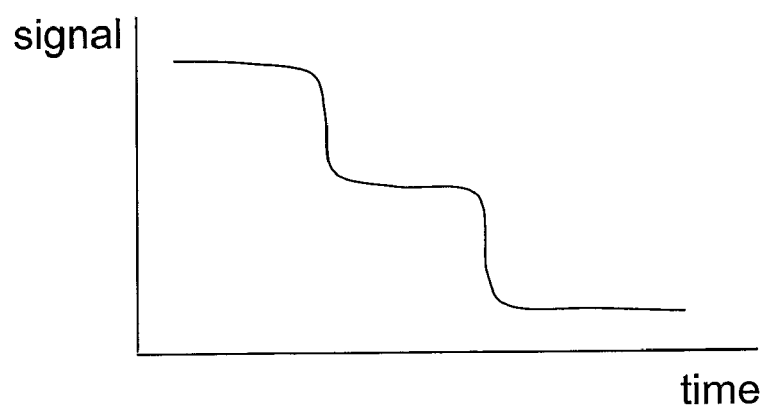
FIG. 15 shows a simplified sketch of signal relaxation as a function of time.
Figure 16:
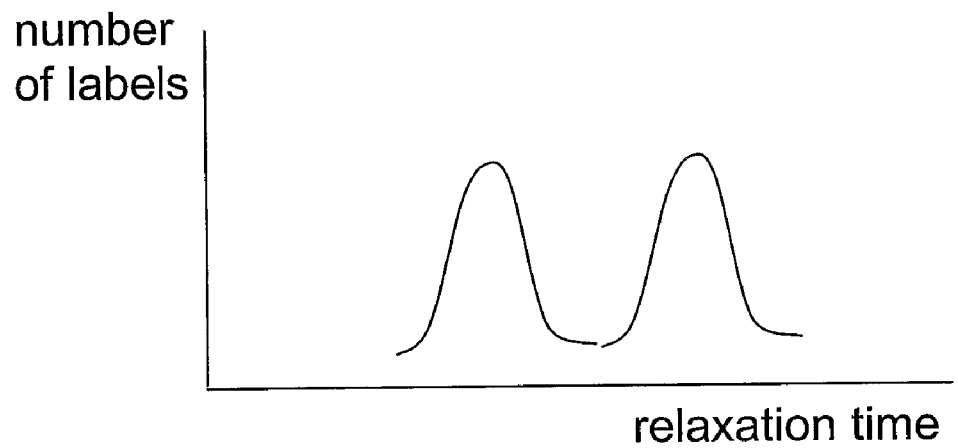
FIG. 16 shows a simplified sketch of a relaxation time distribution for two different types of binding.

Measurement of the thermal rotation relaxation rate can be used to distinguish between labels 11 of different size. Also, measurement of the thermal rotation relaxation rate is an alternative way to distinguish between different types of binding. While binding and unbinding processes are taking place at the surface of the sensor 10, the motional freedom of the magnetic nanoparticle labels 11 is measured to distinguish between different types of binding. One way to do that is by measuring the signal relaxation as a function of time, as illustrated in the graph of FIG. 15. An excitation pulse, which may either be optical, electrical or magnetic, is applied and a signal is recorded as a function of time. The time scale can for example range from 1 ns to 10 s. Subsequently, a distribution of relaxation time is deduced (see FIG. 16), which is indicative of the different types of binding on the surface. For example, bindings of Type 1 will have a shorter relaxation time than the bindings of Type 3 or Type 4 due to the higher rotational freedom in Type 1. The width of the distributions may be determined by the properties of the magnetic nanoparticle label 11, such as for example polydispersity of the labels 11.

A further separation of binding types may be established by applying excitation pulses in different directions, e.g. to distinguish between Type 1 and Type 3a.

It is possible that bindings of Type 1 evolve into bindings of Type 4 with a certain delay. In that case the motion relaxation spectrum should be regularly recorded, so that the total number of bindings of Type 1 can be deduced.

The rotational relaxation can be measured in different ways, e.g. magnetically or optically. Firstly, when the labels have a permanent or inducible magnetic moment, the rotational relaxation may be measured by applying a magnetic field pulse. The labels preferably have a long Neel relaxation time, i.e. a Neel relaxation time that is larger than the rotational relaxation time of the specific binding of Type 1. The relaxation signal of the magnetic labels 11 may be measured by for example magnetoresistive sensors 20, by magnetic induction coils or by superconducting quantum interference devices (SQUIDS) [e.g. Chemla et al., PNAS 97, 14268 (2000)].

Secondly, luminescence polarization (e.g. fluorescence or phosphorescence) may be used to measure label rotation. The particles 11 are magnetic and the optical activity is coupled to the axis of magnetic orientation. For example, optical labels may be included in or on the magnetic nanoparticles 11, with the optical labels being oriented with respect to the magnetic anisotropy axis of the nanoparticles 11. Luminescence polarization detection may be used, with long-lifetime labels such as optically-active rare-earth complexes. Also magneto-optical effects may be used for detection, such as e.g. Kerr rotation, circular dichroism, etc. Also optical detection with two different polarization axes may be used, e.g. the particles 11 may be illuminated with one polarization axis and detection may be performed with another polarization axis. The luminescence lifetime (fluorescence, phosphorescence) has to be comparable with or larger than the label rotation time. In luminescence polarization, the luminescence spectrum generated from the label by polarized light depends upon the state of binding of the label and particularly its rotational freedom.

In a third embodiment of the invention, motional freedom is measured using a one-dimensional (unidirectional) field applied to ferromagnetic particles 11. The motional freedom may be related to the speed of translation in a certain direction through a fluid, e.g. a liquid or a gas. Assuming that at t=0 the magnetic moments of all the particles 11 are at (ϕ=0 and a magnetic field B is applied at angle θ, the particles 11 will rotate toward angle θ according to:

$$\sin(\varphi_B - \varphi_p(t)) = \frac{d\varphi_p(t)}{d(\alpha t)} \qquad (14)$$

The particles will separate into populations with different $\phi_p(t)$ and will consequently have a different arrival time at the angle ϕ or will have different angular spacings from each other.

Preferably, a periodic signal is applied, e.g. a pulse train $B_x+$, $B_x-$, $B_x+$, etc. The magnetic particles 11 will separate into populations with different speeds and different oscillation amplitudes. It will be advantageous to pre-align all magnetic moments, e.g. along the long axis of the sensor strip, so as to get low signals from low-amplitude oscillations. For this purpose a prealigning magnetic field may be applied, either by integrated current wires or external (electro)magnets.

When a sinusoidal magnetic field along the x-axis, $B_x = B_0 \sin(\omega t)$, is applied, the equation of motion becomes:

$$\sin(\omega t)\sin(-\varphi_p(t)) = \frac{d\varphi_p(t)}{d(\alpha_0 t)}, \text{ with } \alpha_0 = \frac{mB_0}{\pi \eta d^3} \qquad (15)$$

and the populations will get a different angle-versus-time dependence as a function of the magnetic moment, the hydrodynamic diameter and the local friction properties (e.g. due to viscous friction and due to local bio-chemical binding).

In a further embodiment, a magnetic torque may be used to put biochemical bonds under stress and break unwanted bonds. Only magnetic particles 11 that are very strongly bound and particles 11 that have sufficient rotational freedom will not be removed.

In a static situation, the force required to counteract an applied torque depends on the location whereon the force acts. For a particle with diameter d, the minimum force required to counteract a magnetic torque (m·B) is given by:

$$F_{min} = \frac{mB}{d/2} \quad (16)$$

In a specific example where $m=10^{-16}$ A·m, B=10 mT and d=100 nm, a minimum force of 20 pN (pico Newton) is required. This force is large enough to break non-specific bonds. In this way, pN forces can be applied using small beads and low magnetic fields. Note that in a translational tweezer, much higher fields and larger beads are required in order to get pN forces.

Bonds can further be tested on rotational freedom by applying a unidirectional rotational stress, i.e. make turns in the same direction. The time-to-bond-breaking gives a measure of the strength of the bond.

With respect to traditional stringency procedures which may for example consist of chemical washing steps, an important advantage of the magnetic method according to the invention is that it can be performed during the binding process, so that the specific signal can be dynamically monitored during the test. This improves the speed of the test and increases the reliability of the outcome.

It has to be noted that an applied torque can act as a single-time, intermittent or even continuous stringency. It can be seen as a physical method to increase the effective dissociation rate ($k_{off}$) of the (bio)chemical interactions that it puts under stress.

Conversely, rotation of labels 11 may be used to optimize the exposure rate in a biochemical assay, in other words the hit-and-stick rate or the effective binding rate ($k_{on}$). This can be applied in two ways. Firstly, when labels 11 are present in solution, rotation of these labels 11 can enhance the interaction and binding rate between the biological material in solution and the surface of the labels 11. This for example applies to the fishing step in an assay, wherein labels 11 are used to bind to specific biological material in a sample solution and/or to extract this material. Secondly, when labels are rotated with respect to another body, e.g. the surface of a biochip or the surface of a cell, the interaction and binding rate between the label and the other body can be enhanced. The increase of the binding rate is particularly important when the surface area of the label is large with respect to the size of the relevant molecular binding region (e.g. paratope, epitope or hybridization matching region) on the label. This is for example the case in low-concentration assays, when a fishing step yields labels with only very little biological material of interest on the label surface. For reference, some calculations on the role of orientation and rotation in biomolecular kinetics can be found in K. S. Schmitz and J. M. Schurr, 'The role of orientation constraints and rotation diffusion in bimolecular solution kinetics', J. Phys. Chem. vol. 76, p. 534 (1972).

The ideal rotation speed is given by an optimal binding rate ($k_{on}$) at acceptable unbinding rate ($k_{off}$) for the biochemical bond that needs to be formed in the given assay time. In other words, the rotation is optimized for sensitivity as well as specificity.

In another embodiment according to the present invention, the above described rotation measurement may be used for distinguishing magnetic nanoparticles 11 with different properties, e.g. different magnetic moment and/or rotational friction properties. Also differences of magnetization lifetime, magnetic anisotropy, or magnetic friction can be used. Thus, rotation spectroscopy may be used to perform bead multiplexing, i.e. distinguish beads with a different intrinsic property. This can be used for label-multiplexed assays, e.g. comparative genomic hybridization. Also this can be used to reduce signals due to less specific or non-specific adsorption and thereby further increase the signal-over-background ratio. It is also possible to distinguish particles or particle clusters with different sizes or different magnetizations. One example is the use of different particles for stringency purposes. Also, a rotation measurement may be used to detect particle clusters or particle chains in the solution and/or on the surface. This can be useful for cluster assays or coagulation assays. Also, in case a fraction of particles show uncontrolled and unwanted coagulation or chain formation, the method according to the invention may be used to distinguish signals of single particles 11 from signals due to coagulated particles, which increases the quantitativeness and reliability of the biological test.

Figure 17:
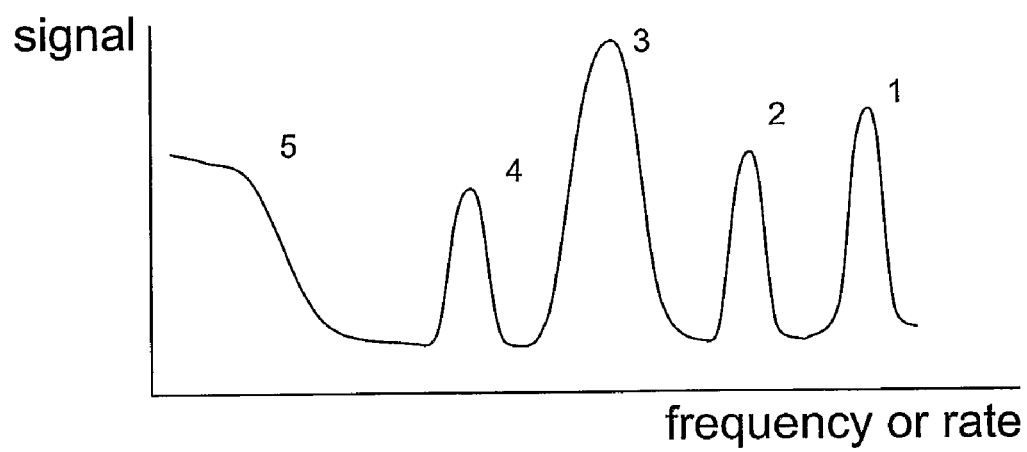
FIG. 17 is an illustrative example of a frequency spectrum.

Although ferromagnetic particles have been described above, other magnetic particles 11 may be used, e.g. particles 11 with a variable angle between the orientation of the particle 11 and the orientation of the magnetic moment on the relevant timescales (e.g. the period of the magnetic field modulation), such as superparamagnetic particles. In yet another embodiment of the invention, a rotating field or a pulsed unidirectional magnetic field may be applied to superparamagnetic particles. Superparamagnetic particles have zero coercive field and a low magnetic anisotropy K and hence $\phi_m \neq \phi_p$. The particles acquire a net magnetic moment only in an applied magnetic field. In that case the applied torque in equation (3) is shared between $\tau_{magn}$ and $\tau_{viscous}$. This can be viewed as a two-slip system, because the magnetization slips with respect to the particle and the particle slips with respect to the environment. Therefore, the angular delay $\phi_B - \phi_m$ depends on the strength of the viscous friction and on the presence of binding to the surface. Note that the rotation frequency of the magnetization is generally unequal to the rotation frequency of the particle itself, as happens in a slipping drive. A measurement of the frequency spectrum can distinguish particles 11 with different magnetic properties and different binding states. An example is sketched in FIG. 17. In the figure, different features can be distinguished which may be attributed to larger or smaller populations of different particles 11, and of particles 11 with different environments and different binding states. For example, peak 1 may for example correspond to non-clustered particles which are not bound to other entities and which can rapidly move or rotate. Peak 2 may be generated by particles 11 that are bound to another entity in a loose manner, e.g. via bonds of Type 1 in FIG. 2. Another peak (e.g. peak 3) can be caused by particles 11 that are clustered to other beads. Peak 4 may be caused by particles 11 with another type of environment, e.g. corresponding to Type 2 in FIG. 2. Feature 5 may be caused by particles 11 with a very strongly hindered motional freedom, e.g. particles 11 that are bound to a surface via multiple interactions. Hence, the position of the peak in the frequency spectrum depends on the type of binding between the bead 11 and the surface of the other entity. It has to be noted that the frequency spectrum of FIG. 17 is only by means of illustration and is not limiting to the invention.

The method according to the different embodiments of the invention uses rotation or motional freedom of magnetic nanoparticles or beads in order to distinguish different bead populations in a biosensor. By applying the method of the invention, it is possible to distinguish between different label-binding populations on a biosensor surface; to discriminate between populations with single specific bonds and populations with multiple less specific or non-specific bonds. Applying the method of this invention leads to an improved signal-to-background ratio and detection limit of biosensors.

The method of the invention may also be applied in a variety of device architectures. The device can for example be a single sensor or an array of biosensors or a so-called bio-chip. Also the method can be applied in a disposable device. For example, the device can be a cartridge or a lab-in-a-device, containing fluid channels, reservoirs, reagents, etc. Also the method can be applied in a disposable pipette tip or inside an affinity column. The method can also be applied in a well or in multiple wells, e.g. a well-plate or a microtiter plate.

An advantage of the method according to the invention is that while binding and unbinding processes are taking place on the surface, the motional freedom of the labels is measured to distinguish between different types of binding.

The methods described in this application may also be used for a molecular assay and for the detection of micro-organisms, cells, cell fragments, tissue extracts etc.

In addition to the rotational forces, magnetic field gradients may be applied. These will generate a translational force, e.g. to stretch biochemical bonds.

There are several assays that can make use of the above described label-rotation methods. One is an assay in which a label 11 binds or unbinds and thereby changes its rotation properties, where the binding or unbinding depends on the presence of specific biological material in the sample. Examples are binding assays, competition assays, inhibition assays, displacement assays.

Another type of assay operates similar to a magnetic tweezer, in which a magnetic particle 11 is bound to another body (e.g. a solid surface) by a biological linker. As an example, the linker can be a nucleic-acid molecule which is mechanically stressed by a magnetically-applied stretching force or which is made to interact with enzymes from solution (e.g. restriction enzymes or DNA repair enzymes). In the traditional magnetic-tweezer instrument the xyz-position and the motion of the magnetic particle 11 indicate the state of the biological linker and how it interacts with its surroundings. With the methods of this invention, a magnetic tweezer can be made in which the xyz-position as well as the rotation of the magnetic particle 11 or magnetic particles 11 are detected by on-chip magnetic sensors. During the assay, translational as well as rotational magnetic forces can be applied in three dimensions. This can be done in a compact and versatile instrument, for assays wherein material from solution is analyzed via interactions with a biological moiety that links a magnetic particle 11 or magnetic particles 11 to a magnetic sensor 10. An advantage of a rotational tweezer with respect to a z-force tweezer is that smaller beads can be used and higher-frequency properties can be measured.

Another class of assays in which particle rotation can be used, are assays where a particle initially has a hindered rotation and in which the intervention of other material enhances the rotational freedom. For example, a particle 11 connected to a molecular beacon (a hairpin-like nucleic acid which opens up when it hybridizes to a complementary nucleic-acid strand) can have a hindered rotation in the closed state and an enhanced rotational freedom in the open state of the beacon. Also, a probe molecule could change its shape upon binding of a target molecule, thereby changing the rotational freedom of an attached or neighboring magnetic particle. Also, an enzyme could cleave part of the linker molecule, thereby enhancing the rotational freedom of the particle.

In another class of assays, the rotational freedom of a particle 11 is reduced by interactions with a molecular species. For example, a particle that is linked to a body by single-stranded DNA will loose part of its rotational freedom when the linker becomes double-stranded DNA by hybridization of a complementary strand. This is due to the mechanical stiffness of double-stranded DNA. Also, due to the binding of a target molecule, a particle may change its distance to large bodies in the vicinity (e.g. a surface), thereby changing the friction and rotational freedom.

In another class of assays, the rotation is driven by biological activity, e.g. enzymes and enzyme substrates cause rotation of molecular or cellular species. An example of rotational enzymes are e.g. the helicases. The rotation of the particle 11 can be probed and detected magnetically.

Another class of assays makes use of cells. Magnetic particles 11 bind to the cell surface or go into the cell, thereby changing their rotation properties. Or particles 11 that are already present change their rotation properties due to interactions with other biological molecules. The cells can be attached to a sensor surface or can be present in a solution.

Note that the above methods can be applied for ex-vivo diagnostics as well as for in-vivo diagnostics, e.g. on cells, tissue, organisms, and living bodies. When applied for in-vivo diagnostics, e.g. in the form of molecular imaging, care should be taken to avoid interference between magnetic actuation and magnetic detection, e.g. by using an external magnetic field for particle rotation and an optical system for detection of rotation, or by using time-separated actuation and detection (e.g. switched-field magnetic resonance).

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A sensor device for distinguishing a specific binding from a less specific binding between at least one polarizable or polarized nanoparticle label and a surface of another entity, the sensor device comprising:
   at least one electric or magnetic field generator for applying an electric or a magnetic field to a sample fluid containing polarized or polarizable nanoparticle labels;
   at least one magnetic sensor element; and
   a detector for detecting a parameter related to nanoparticle rotational or motional freedom while the nanoparticle labels are attached to the surface for distinguishing a specific binding from a less specific binding between said nanoparticle labels and the surface of the other entity, wherein the electric or magnetic field generator generates a rotating magnetic field.

2. The sensor device of claim 1, wherein the electric or magnetic field generator is located on the sensor device.

3. The sensor device of claim 1, wherein the electric or magnetic field generator is a two-dimensional wire structure.

4. The sensor device of claim 1, wherein the magnetic sensor element is one of an AMR, a GMR or a TMR sensor element.

5. The sensor device of claim 1, further comprising two electric or magnetic field generator positioned at each side of one magnetic sensor element.

6. The sensor device of claim 1, wherein the sensor device is positioned in between two current lines.

* * * * *